United States Patent
Christman et al.

(10) Patent No.: US 11,440,992 B2
(45) Date of Patent: Sep. 13, 2022

(54) OXIME CROSS-LINKED BIOCOMPATIBLE POLYMER HYDROGELS AND METHODS OF USE THEREOF

(71) Applicant: The Regents of the University of California, Oakland, CA (US)

(72) Inventors: Karen Christman, San Diego, CA (US); Masaki Fujita, San Diego, CA (US); Michael Madani, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/497,831

(22) PCT Filed: Mar. 27, 2018

(86) PCT No.: PCT/US2018/024503
§ 371 (c)(1),
(2) Date: Sep. 26, 2019

(87) PCT Pub. No.: WO2018/183284
PCT Pub. Date: Oct. 4, 2018

(65) Prior Publication Data
US 2020/0102422 A1 Apr. 2, 2020

Related U.S. Application Data

(60) Provisional application No. 62/477,046, filed on Mar. 27, 2017.

(51) Int. Cl.
*C08G 65/48* (2006.01)
*A61L 31/14* (2006.01)
*A61L 31/16* (2006.01)
*A61L 31/06* (2006.01)

(52) U.S. Cl.
CPC .............. *C08G 65/48* (2013.01); *A61L 31/06* (2013.01); *A61L 31/145* (2013.01); *A61L 31/16* (2013.01); *A61L 2400/06* (2013.01)

(58) Field of Classification Search
CPC ... A61L 24/00; A61L 31/145; A61L 2300/236
See application file for complete search history.

(56) References Cited

U.S. PATENT DOCUMENTS

| 9,289,449 B2 | 3/2016 | Sershen et al. |
| 2012/0003888 A1* | 1/2012 | Lee .................. C08G 65/33396 442/1 |

FOREIGN PATENT DOCUMENTS

| EP | 1967220 A2 | 9/2008 | |
| KR | 101436466 B1 | 9/2014 | |
| WO | 2016/010484 A1 | 1/2016 | |
| WO | WO-2016010484 A1 * | 1/2016 | ........... A61L 24/043 |
| WO | 2016/094535 A1 | 6/2016 | |
| WO | WO-2016094535 A1 * | 6/2016 | .............. C08F 16/06 |

OTHER PUBLICATIONS

Dictionary.com, "adhere", 6 pages.*
Dictionary.com "bind" 7 pages.*
PCT International Search Report and Written Opinion for PCT Application No. PCT/US2018/024503 dated May 24, 2018 (12 pages).

* cited by examiner

*Primary Examiner* — Kyle A Purdy
(74) *Attorney, Agent, or Firm* — Eversheds Sutherland (US) LLP

(57) ABSTRACT

Methods and hydrogels for preventing or reducing cellular adhesion and protein adsorption to a tissue (e.g. cardiac tissue) are disclosed. The hydrogels generally include at least three component polymers, a first polymer including an aminooxy group, a second polymer including a reactive oxo group, that are cross-linked by oxime bonds and a third polymer including a catechol group, that causes better retention on the cardiac tissue. The hydrogels are suitable for binding to and coating a tissue or cell. The hydrogels operate to reduce cellular adhesions and protein adsorption to the tissue or cell.

35 Claims, 17 Drawing Sheets

| No. | Category | Polymer | MW | Functionalization ratio (%) | Functionalization Group number |
|---|---|---|---|---|---|
| 1 | Ald- | Ald-8PEG10k | 11 k | 97 | 8 |
| 2 | | Ald-8POSS-PEG10k | 13 k | 85 | 7 |
| 3 | | Ald-8POSS-PEGPPGPEG10k | 16 k | 76 | 6 |
| 4 | | Ald-8PEG5k | 6 k | 60$^{*1}$ | 5 |
| 5 | | Ald-8POSS-PEG5k | 7 k | 91 | 7 |
| 6 | AO- | AO-8PEG10k | 10 k | 83 | 7 |
| 7 | | AO-8PEG5k | 5 k | 76 | 6 |
| 8 | Cat- | Cat-8PEG10k | 11 k | 92 | 7 |
| 9 | | CatAld-8PEG10k) | 11 k | 70 | 6(3/3) |

FIGURE 7

| No. | Category 1 | Category 2 | Hydrogel | Polymer Combination | Ratio (wt/wt) |
|---|---|---|---|---|---|
| 1 | High MW | AA | 10k/10k | Ald-8PEG10k/AO-8PEG10k | 1/1 |
| 2 | | AA | P10k/10k | Ald-8POSS-PEG10k/AO-8PEG10k | 1/1 |
| 3 | | AA | PPP10k/10k | Ald-8POSS-PEGPPGPEG10k/AO-8PEG10k | 1/1 |
| 4 | | AACat | 10k/10k/Cat10 | Ald-8PEG10k/AO-8PEG10k/Cat-8PEG10k | 1/1/1 |
| 5 | | AACat | CatAld10k/10k | CatAld-8PEG10k/AO-8PEG10k | 1/1 |
| 6 | Low MW | AA | 5k/5k | Ald-8PEG5k/AO-8PEG5k | 1/1 |
| 7 | | AA | P5k/5k | Ald-8POSS-PEG5k/AO-8PEG5k | 1/1 |
| 8 | Mix MW | AA | 10k/5k | Ald-8PEG10k/AO-8PEG5k | 1/1 |
| 9 | | AA | 5k/10k | Ald-8PEG5k/AO-8PEG10k | 1/1 |

FIGURE 8

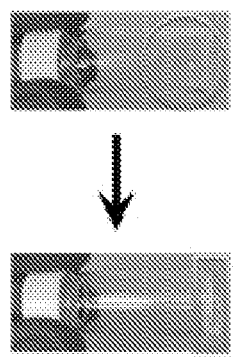

FIGURE 9A

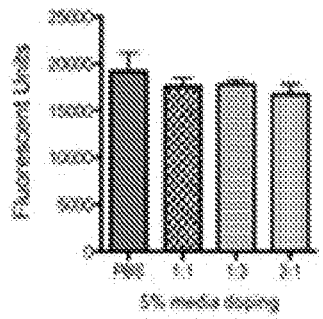
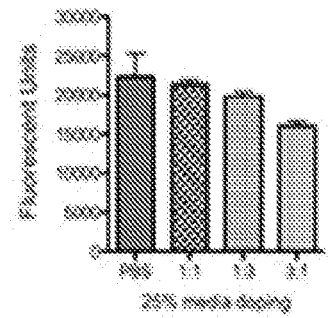
FIGURE 14A            FIGURE 14B
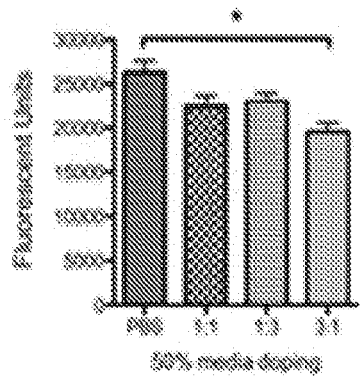
FIGURE 14C
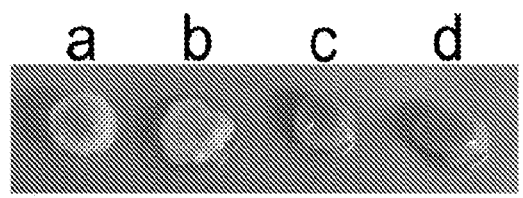
FIGURE 15

| Score | Physiological condition |
|---|---|
| 0 | No adhesion |
| 1 | Mild and filmy; adhesion can be easily pulled apart |
| 2 | Moderate adhesion; requires dissection with sharp tool |
| 3 | Dense adhesion; requires careful dissection; little to no vascularization |
| 4 | Dense adhesion; requires careful dissection; strong degree of vascularization |

OXIME CROSS-LINKED BIOCOMPATIBLE POLYMER HYDROGELS AND METHODS OF USE THEREOF

CROSS REFERENCE TO RELATED APPLICATIONS

This application claims the priority benefit of PCT/US2018/024503 filed on Mar. 27, 2018 which claims the priority benefit to U.S. Provisional Patent Application No. 62/477,046, filed Mar. 27, 2017, the entire contents of which are incorporated by reference.

GOVERNMENT SPONSORSHIP

This invention was made with government support under grant No TR000100 awarded by the National Institute of Health. The government has certain rights in the invention.

FIELD OF THE INVENTION

The present disclosure relates generally to hydrogels and methods of use thereof and, more particularly, oxime cross-linked biocompatible polymer hydrogels.

BACKGROUND OF THE INVENTION

As a result of the healing process that follows surgery, complications frequently arise due to the natural tendency of the body to form adhesions. Postsurgical adhesions negatively impact patient comfort and organ function.[3-5] Postsurgical adhesions are particularly problematic for cardiac surgery patients. Many patients that have cardiac surgery, especially pediatric patients, must undergo reoperative procedures during their lifetime.[6-8] The presence of postsurgical cardiac adhesions increases the difficulty and risks of the reoperative procedure due to increased surgery times and potential hemorrhaging upon gaining re-access to the heart.[8]

Two main approaches exist for reducing or attempting to prevent cardiac adhesions: pharmacological therapy and physical barriers. Drugs that prevent or reverse adhesion processes disrupt biochemical pathways of inflammation and fibrin deposition (see e.g., WO 2013135647 A1). Unfortunately, these processes are also vital for wound healing. Achieving adequate drug concentration at the site of action, especially for ischemic tissues, is also challenging.

A more viable approach is the use of a physical barrier after surgery to prevent fusion of the heart to surrounding tissues. The barriers can be either preformed membranes (see e.g., US 20120088832 A1, CA 2513640 C, and WO 2013032201 A2) or injectable hydrogels (fast gelling liquids) (see e.g., EP 1967220 A2, EP 2470223 A2 and U.S. Pat. No. 5,874,500 A). Preformed anti-adhesive materials need to be cut before application to the tissue, and must be sutured into place to prevent slippage. Injectable hydrogels allow the freedom of applying material where needed by "painting" or spraying the precursor components and are capable of quickly forming a protective gel over the surface of the tissue. Therefore, a promising method to prevent postsurgical adhesions is to coat the tissue with a fast gelling polymer to prevent the susceptible tissue from adhering to other nearby tissue organs.[3]

Materials that bind to tissues are widely used in clinical procedures; including abdominal, brain, spine, and cardiac surgeries. These materials are used to achieve homeostasis, seal tissues, deliver exogenous substances locally, or prevent postsurgical adhesions. The safety and efficacy of these materials is directly impacted by the purity of the components and mode of material formation.[1,2] For synthetic materials, the cross-linking chemistry and subsequent degradation products can dramatically impact the biocompatibility of the material.[1] There are, however, only a limited number of materials that prevent postsurgical adhesions in a clinical setting. Further, while a variety of different materials have been investigated in animals and humans, no materials to date, have been capable of preventing adhesion formation post-cardiac surgery.

The mechanism of material adherence to tissue can be divided into two modes, non-covalent and covalent. Non-covalent materials include collagen, fibrin, and gelatin as well as ionic and thermoresponsive polymers. While these materials generally exhibit good biocompatibility, they are rapidly degraded or removed from the tissue surface in vivo due to the non-covalent association. Additionally, the protein-based materials contain ligands that promote cellular attachment, which is not ideal for preventing postsurgical adhesions that are the result of inflammation.[3,9]

Covalent attachment can be achieved through two different approaches. One approach uses radical polymerization or anionic polymerization (cyanoacrylates). However, due to the polymerizable functional groups these systems have exhibited toxicity in vivo.[1,10] The other covalent approach relies on reaction with nucleophilic functional groups present on the tissue surface by using epoxides, activated carboxylic acids, or aldehydes. This approach is attractive since the materials can be synthesized with a desired number of functional groups and molecular weights to tune tissue reactivity, gelation times, and facilitate clearance from the body upon degradation.[1]

From a chemistry perspective, adhesion prevention is challenging, especially in a cardiac surgery setting. The material should be easily applied, gel rapidly (<5 min) on the wet tissue surface, remain on the tissue for at least 2 weeks to overcome the initial inflammatory response post-surgery, exhibit minimal swelling (to not impede cardiac function), and be biocompatible. This means that the pre-gel materials must be capable of reacting quickly and efficiently with themselves as well as with tissue, and the cross-linking functional groups must be biocompatible. Once gelled, the material must prevent cellular adhesion to prevent fibrin deposition from infiltrating cells, since this leads to adhesions.[3]

Oxime chemistry has been successfully used in a variety of in vitro and in vivo applications,[11] and PEG-coated surfaces have shown to minimize protein adsorption[12] and cellular adhesion.[13] It has been demonstrated that oxime chemistry is biocompatible, chemospecific, and bioorthogonal.[11,14] (see e.g., WO 2016094535 A1) However, preliminary in vivo studies in a rat model showed that retention on the rat heart was not optimal, which did not exhibit consistent results with adhesion prevention in two weeks. What is needed are novel PEG-based injectable hydrogels with bio-inspired adhesive material which has been normally used in biomedical applications as tissue adhesives.

Therefore, what are needed are improved methods and compositions for use as an anti-adhesion barrier with higher retention ability on the heart. It would be desirable to employ a new chemistry that results in rapid forming hydrogels capable of adhering to tissue surfaces. The present invention addresses these and other related needs in the art.

SUMMARY OF THE INVENTION

In some embodiments, an oxime cross-linked biocompatible hydrogel is provided, which includes: a first polymer comprising an aminooxy group selected from a hydroxyl amine and an alkoxy amine polymerized to a second polymer comprising a reactive oxo group, wherein the hydrogel has a surface comprising a surface oxo group that reversibly binds an amine group on a living tissue surface to form an imine. In some embodiments, the reactive oxo group and the surface oxo group are ketones. In some embodiments, the reactive oxo group and the surface oxo group are aldehydes. In some embodiments, the first polymer and the second polymer are each selected from the group consisting of poly(ethylene glycol), multi-arm poly(ethylene glycol), hyaluronic acid, alginate, dextran, carboxymethylcellulose, cellulose, poly(vinyl alcohol), multi-arm polyhedral oligomeric silsesquioxanes or combinations thereof.

In some embodiments, a method of administering an oxime cross-linked bioadhesive hydrogel to a tissue for use as an in-situ anti-adhesion barrier is provided, the method comprising: administering to a living tissue of an individual an effective amount of a combination of a first polymer comprising an aminooxy group selected from a hydroxyl amine and an alkoxy amine, and a second polymer comprising a reactive oxo group, wherein the first polymer and second polymer are mixed and react to form an oxime cross-linked biocompatible hydrogel proximate to the tissue, wherein the hydrogel has a surface comprising a surface oxo group, and wherein the surface oxo group reversibly binds a surface amine on the tissue to form an imine. In some embodiments, the oxime cross-linked biocompatible hydrogel is formed in about 5 minutes or less. In some embodiments, the first polymer and the second polymer are administered by spraying, dripping, or painting the first polymer and the second polymer directly onto the tissue. In some embodiments, a third polymer is included in the hydrogels system, wherein the polymer is a bio-inspired material which causes adhesion on the heart.

BRIEF DESCRIPTION OF THE DRAWINGS

Those of skill in the art will understand that the drawings, described below, are for illustrative purposes only. The drawings are not intended to limit the scope of the present teachings in any way.

FIG. 7. Polymer inventory.

FIG. 8. Hydrogel inventory.

FIGS. 9A-9B. Formation of fast-gelling PEG hydrogels. FIG. 9A: upon mixing of ald-PEG and AO-PEG, transparent gels were formed in water at 25° C. FIG. 9B: tunable gelation times based upon polymer concentration (mg/mL).

FIG. 10A: percent mass loss over time in PBS at 37° C. for hydrogels mixing ald-PEG with AO-PEG (MW ca. 10 k). FIG. 10B: percent mass loss over time in PBS at 37° C. for hydrogels mixing ald-PEG with AO-PEG (MW ca. 5 k). FIG. 10C: percent mass loss over time in PBS at 37° C. for hydrogels mixing ald-PEG and ald-POSS-PEG with AO-PEG. FIG. 10D: percent mass loss over time in PBS at 37° C. for hydrogels including catechol-PEG.

FIGS. 14A-14C. Metabolic activity of 3T3 fibroblasts after 24 h with elution product doped media (functional group ratio is aldehyde:aminooxy and * is $p<0.05$).

FIG. 15. Tissue sections: (a) aorta, (b) adipose, (c) atrium, and (d) ventricle coated with hydrogels mixing ald-PEG with AO-PEG with 1:1 aldehyde:amino-oxy and coated with hydrogels mixing ald-PEG and catechol-PEG with AO-PEG after 2 weeks.

(FIG. 16A) aorta, (FIG. 16B) adipose, (FIG. 16C) atrium, and (FIG. 16D) ventricle coated with hydrogels FIGS. 17A-17B. Representative images of the epicardial surface after cardiac abrasions surgery on rats.

DETAILED DESCRIPTION OF THE INVENTION

Figure 1:
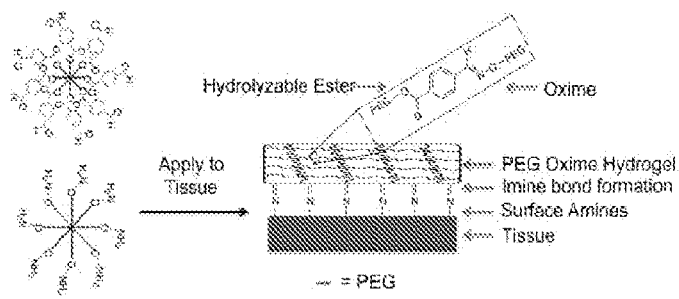
FIG. 1. Formation of oxime cross-linked PEG-hydrogel onto tissue surface.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. DEFINITIONS

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It is understood that aspects and embodiments of the invention described herein include "consisting" and/or "consisting essentially of" aspects and embodiments.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "hydrogel" refers to a water-swellable polymeric matrix comprising a network of macromolecules held together by covalent cross-links that can absorb water to form an elastic gel.

The term "cross-link" refers to a bond or chain of atoms attached between and linking two different polymer chains.

The term "PEG" as used herein refers to poly(ethylene glycol).

The term "multi-arm PEG" refers to a branched poly(ethylene glycol).

The term "PVA" as used herein refers to poly(vinyl alcohol).

The term "AO" refers to an aminooxy group.

The term "RO" refers to a reactive oxo group.

The term "Ald" refers to an aldehyde group.

The term "DOPA" refers to catechol dopamine

The term "AO-PEG" refers to a poly(ethylene glycol) that is derivatized (i.e. chemically modified) to contain an aminooxy group.

The term "RO-PEG" refers to a poly(ethylene glycol) that is derivatized (i.e. chemically modified) to contain a reactive oxo group.

The term "RO-PEG-PVA" refers to a poly(ethylene glycol)-poly(vinyl alcohol) copolymer that is derivatized (i.e. chemically modified) to contain a reactive oxo group.

The term "ald-PEG" refers to a poly(ethylene glycol) that is derivatized (i.e., chemically modified) to contain an aldehyde group.

The term "ald-PEG-PVA" refers to a poly(ethylene glycol)-poly(vinyl alcohol) copolymer that is derivatized (i.e. chemically modified) to contain an aldehyde group.

The term "POSS" refers to a polyhedral oligomeric silsesquioxanes.

The term "multi-arm POSS" refers to a branched polyhedral oligomeric silsesquioxanes.

A "branched" polymer refers to a polymer having one or more branch points ("arms"), and includes star, dendritic, comb, and hyperbranched polymers. In some embodiments, branched polymers can have between 3 and 100 arms.

A "star" polymer refers to a polymer having a central branch point, which may be a single atom or a chemical group, from which arms emanate.

It should be recognized that branched or multi-arm polymers can be a somewhat heterogeneous mixture having a distribution of species with different numbers of arms. When a multi-arm polymer has a distribution of species having different numbers of arms, it can be referred to based on the average number of arms in the distribution. For example, in one embodiment, a hydrogel precursor is an 8-arm star PEG (each arm being terminated by aminooxy group) which comprises a mixture of multi-arm star PEG, some having less than and some having more than 8 arms; however, the multi-arm star PEG in the mixture have an average of 8 arms. Therefore, the terms "8-arm", "6-arm", "4-arm", "3-arm", and the like, as used herein to refer to multi-arm polymers, should be construed as referring to a homogeneous mixture or a heterogeneous mixture having a distribution of species with different numbers of arms, in which case the number of arms recited refers to the average number of arms in the mixture.

The term "tissue" refers to any biological tissue in individual humans or animals.

The term "prevent" is meant to indicate postponing, suppressing, or reducing the risk of developing or recurrence of a disease, disease symptom, and/or medical condition.

B. OXIME CROSS-LINKED HYDROGELS

Disclosed herein are oxime cross-linked hydrogel tissue adhesives formed by reacting a first polymer (i.e. a first precursor) comprising an aminooxy group with a second polymer (i.e. a second precursor) comprising a reactive oxo group, and including a third polymer comprising a catechol group. The hydrogel may be useful as a tissue adhesive or sealant for medical applications including, but not limited to, prevention of undesired post-surgical tissue adhesions. The hydrogel can act as a barrier that isolates organs or tissue from each other for a predetermined period, depending on the absorption and/or degradation profile of the hydrogel.

Hydrogel Precursors and Hydrogels

In general, at least two types of hydrogel precursors are provided. A first hydrogel precursor comprises a polymer terminated with an aminooxy group. Various aminooxy groups suitable for use in the present invention are well known to those of ordinary skill in the art. Exemplary aminooxy groups include hydroxyl amines, alkoxyl amines, and the like. A second hydrogel precursor comprises a polymer terminated with a reactive oxo group. Various reactive oxo groups suitable for use in the present invention are well known to those of ordinary skill in the art. Exemplary reactive oxo groups include ketones, aldehydes, and the like.

Polymers suitable for use as hydrogel precursors can include poly(ethylene glycol), branched or multi-arm poly(ethylene glycol), copolymer of poly(ethylene glycol) and poly(propylene glycol), multi-arm copolymer of poly(ethylene glycol) and poly(propylene glycol), hyaluronic acid, alginate, dextran, carboxymethylcellulose, cellulose, poly(vinyl alcohol), and their copolymers. In some embodiments, hydrogel precursors comprise a multi-arm polymer.

In some embodiments, hydrogel precurusors comprise a branched polymer. In some embodiments, hydrogel precursors comprise a star polymer. In some embodiments, hydrogel precursors comprise a polyhedral oligomeric silsesquioxanes. Polymers suitable for use as hydrogel precursors are either available commercially or may be prepared using methods known in the art. In some embodiments, the polymers used as hydrogel precursors have a molecular weight of about 1,000 g/mol to about 50,000 g/mol.

In some embodiments, hydrogel precursors comprise a multi-arm poly(ethylene glycol) having 3, 4, 6, or 8 arms terminated with aminooxy groups (e.g. hydroxyl amines, alkoxyl amines, and the like). In some embodiments, a hydrogel precursor is an eight-arm poly(ethylene glycol) having eight arms terminated by aminooxy groups (e.g. hydroxyl amines, alkoxyl amines, and the like). In some embodiments, the multi-arm poly(ethylene glycol) having 3, 4, 6, or 8 arms terminated with aminooxy groups (e.g. hydroxyl amines, alkoxyl amines, and the like) has a molecular weight of about 10,000 g/mol or less or 5,000 g/mol or less.

In some embodiments, hydrogel precursors comprise a multi-arm poly(ethylene glycol) having 3, 4, 6, or 8 arms terminated with reactive oxo groups (e.g. ketones, aldehydes, and the like). In some embodiments, a hydrogel precursor is an eight-arm poly(ethylene glycol) having eight arms terminated by reactive oxo groups (e.g. ketones, aldehydes, and the like). In some embodiments, the multi-arm poly(ethylene glycol) having 3, 4, 6, or 8 arms terminated with reactive oxo groups (e.g. ketones, aldehydes, and the like) has a molecular weight of about 10,000 g/mol or less or 5,000 g/mol or less.

In some embodiments, hydrogel precursors comprise a multi-arm poly(ethylene glycol)-poly(vinyl alcohol) copolymer having 3, 4, 6, or 8 arms terminated with reactive oxo groups (e.g. ketones, aldehydes, and the like). In some embodiments, a hydrogel precursor is an eight-arm poly(ethylene glycol)-poly(vinyl alcohol) copolymer having eight arms terminated by reactive oxo groups (e.g. ketones, aldehydes, and the like). In some embodiments, the multi-arm poly(ethylene glycol)-poly(vinyl alcohol) copolymer having 3, 4, 6, or 8 arms terminated with reactive oxo groups (e.g. ketones, aldehydes, and the like) has a molecular weight of about 50,000 g/mol or less, 10,000 g/mol or less, or 5,000 g/mol or less.

The oxime cross-linked hydrogels disclosed herein can swell minimally after deposition. Swelling of a hydrogel relates to its change in volume (or weight) between the time of its formation when cross-linking is effectively complete and a time after at which point the hydrogel may be reasonably assumed to have achieved its equilibrium swelling state. In some embodiments, the hydrogel may achieve an equilibrium swelling state in about 24 hours or less. In some embodiments, the hydrogel weight and/or volume increases no more than about 0% to about 10% or to about 50% upon exposure to a physiological solution relative to a weight and/or volume of the hydrogel at the time of formation. In some embodiments, the hydrogel has less than a 20%, 30%, 40%, 50%, 60%, 70%, 75%, 80%, 85%, 90%, 95%, or 100% increase in volume when swollen. In some embodiments, cross-linking is effectively complete within about ten minutes. In some embodiments, the hydrogel gels (cross-linking is effectively complete) in about less than 30 seconds, 1 minute, 1.5 minutes, 2 minutes, 2.5 minutes, 3.0 minutes, 3.5 minutes, 4.0 minutes, 4.5 minutes, 5 minutes, or 10 minutes.

A hydrogel formed in a location where it is constrained is not necessarily a low-swelling hydrogel. For instance, a swellable hydrogel created in a body may be constrained from swelling by its surroundings but nonetheless may be a highly swellable hydrogel as evidenced by measurements of its swelling when unconstrained.

In some embodiments, the hydrogel comprises between about 25 mg/mL polymer and about 200 mg/mL polymer in final concentration of hydrogels.

In some embodiments, the hydrogel has a storage modulus of less than 1 kPA, 2 kPA, 3 kPA, 4 kPA, 5 kPA, 10 kPA, or 20 kPA.

In some embodiments, the hydrogel resorbs and/or degrades over a period of time. In some embodiments, the hydrogel takes longer than 5 days, 1 week, or 2 weeks to resorb and/or degrade. In some embodiments, the hydrogel takes less than 1, 2, or 3 months to resorb and/or degrade.

In some embodiments, the polymer precursors and/or hydrogel are biocompatible, biodegradable, and/or substantially water soluble.

In some embodiments, the hydrogel cross-linking can be reversed. In some embodiments, hydrogel cross-linking is reversed with the addition of free aminooxy groups (e.g. hydroxyl amines and alkoxy amines) or free reactive oxo groups (e.g. ketones, aldehydes, and the like).

In some embodiments, the polymer precursors and/or hydrogel further comprises a bioactive agent or an antimicrobial. A bioactive agent can include any drug, pharmaceutical compound, or molecule (e.g. small molecule, protein, peptide, RNA fragments, nucleic acid, inorganic and organic biologically active compounds, etc.) having a therapeutic effect. Suitable bioactive agents are well known in the art (see e.g. the United States Pharmacopeia (USP), Physician's Desk Reference, and the like). In some embodiments, the bioactive agent may be an anti-inflammatory agent, an antibacterial agent, and/or a healing promoter.

In some embodiments, the physicochemical properties of the hydrogel including gelation time, gelation rate, lifespan, degradation, mechanical strength and/or water content can be controlled and are tunable based upon the molecular weight of the polymer precursors used, the weight percent of the polymer precursors, the number of cross-linking sites or arms on the polymers, and other parameters known in the art. In some embodiments, increasing the number of cross-linking sites or arms increases the gelation rate. In some embodiments, decreasing the molecular weight of polymers increases the gelation rate. In some embodiments, the hydrogel contains hydrolysable ester linkages that can be manipulated to tune the rate of hydrolysis of the hydrogel post-gelation.

Hydrogel Delivery

The oxime cross-linked hydrogels disclosed herein may be used to form a coating on an anatomical site or tissue of a living organism. In some embodiments, hydrogel precursors are components of aqueous solutions or dispersions. In some embodiments, a first aqueous solution or dispersion comprises a polymer terminated with an aminooxy group and a second aqueous solution or dispersion comprises a polymer terminated with a reactive oxo group. In some embodiments, a polymer including catechol groups is premixed with a polymer terminated with a reactive oxo group. The optimal concentrations of the polymers in the two aqueous solutions or dispersions depends on the intended application, and can be readily determined by one skilled in the art using routine experimentation.

For use on living tissue, in some embodiments, it is preferred that the first aqueous solution or dispersion and the second aqueous solution or dispersion be sterilized to prevent infection. Any suitable sterilization method known in the art that does not degrade the components may be used. Exemplary sterilization methods can include using heat, ethylene oxide sterilization, ultra-violet radiation, or ultra-filtration through a pore membrane.

The aqueous solution(s) or dispersion(s) may further comprise various additives depending on the intended application. The amount of the additive used depends on the particular application and may be readily determined by one skilled in the art using routine experimentation. For example, the aqueous solution(s) or dispersion(s) may comprise one or more additives such as pH modifiers, viscosity modifiers, antimicrobials, colorants, surfactants, and bioactive agents.

The aqueous solution(s) or dispersion(s) may include at least one pH modifier to adjust the pH. Suitable pH modifiers are well known in the art. The pH modifiers may be acidic or basic compounds.

The aqueous solution(s) or dispersion(s) may include at least one viscosity modifier. In some embodiments, the aqueous solution(s) or dispersion(s) include at least one thickening or thinning agent. Suitable thickening or thinning agents are well known in the art.

The aqueous solution(s) or dispersion(s) may include at least one antimicrobial agent. Suitable antimicrobial agents are well known in the art. Examples of antimicrobials that may be suitable include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may include at least one colorant to enhance the visibility of the solution(s) or dispersion(s). Suitable colorants can include, but are not limited to, dyes, pigments, and natural coloring agents.

The aqueous solution(s) or dispersion(s) may include at least one surfactant. Surfactant, as used herein, refers to a compound that lowers the surface tension of water. Suitable surfactants are well known in the art.

The aqueous solution(s) or dispersion(s) may optionally include at least one bioactive agent. A bioactive agent can include any drug, pharmaceutical compound, or molecule (e.g. small molecule, protein, peptide, RNA fragments, nucleic acid, inorganic and organic biologically active compounds, etc.) having a therapeutic effect. Suitable bioactive agents are well known in the art (see e.g. the United States Pharmacopeia (USP), Physician's Desk Reference, and the like). In some embodiments, the bioactive agent may be an anti-inflammatory agent and/or a healing promoter.

The aqueous solution(s) or dispersion(s) may be applied to an anatomical site or tissue of a living organism to form a coating in any number of ways. In some embodiments, once a first aqueous solution or dispersion comprising a polymer terminated with an aminooxy group and a second aqueous solution or dispersion comprising a polymer terminated with a reactive oxo group are applied to a site, they cross-link to form a hydrogel, a process that typically takes about 2 seconds to about 10 minutes.

In some embodiments, two aqueous solutions or dispersions are applied to a site simultaneously or sequentially using any suitable means including, but not limited to, spraying, brushing or painting (e.g. with a cotton swab or brush), dripping, or extrusion using a pipette or a syringe which may be fitted with a hypodermic needle, a nozzle, or tubing to help direct fluid flow. The solutions or dispersions may be applied in any order when applied sequentially. In some embodiments, the solutions or dispersions are further mixed at the site. The further mixing can be done using any suitable means well known in the art such as by using a device such as a cotton swab, a spatula, a brush, or the tip of a pipette or syringe.

In some embodiments, two aqueous solutions or dispersions are mixed before application to a site. The resulting mixture is then applied to the site before the mixture completely cures. The resulting mixture can be applied to a site using any suitable means including, but not limited to, spraying, brushing or painting (e.g. with a cotton swab or brush), dripping, or extrusion using a pipette or a syringe which may be fitted with a hypodermic needle, a nozzle, or tubing to help direct fluid flow.

In some embodiments, two aqueous solutions or dispersions are applied to a site simultaneously where they mix to form a hydrogel.

In some embodiments, two aqueous solutions or dispersions are contained in separate barrels of a double-barrel syringe. In this way the two aqueous solutions or dispersions are applied simultaneously to a site with the syringe. Suitable double-barrel syringe applicators are known in the art.

In some embodiments, two aqueous solutions or dispersions are applied to a site using a spray device.

Hydrogel Kits

In some embodiments, a kit is provided. In some embodiments, the kit comprises at least one hydrogel precursor having a polymer terminated with an aminooxy group and at least one hydrogel precursor having a polymer terminated with a reactive oxo group. In some embodiments, the kit comprises a first aqueous solution or dispersion having a polymer terminated with an aminooxy group and a second aqueous solution or dispersion having a polymer terminated with a reactive oxo group. Each of the aqueous solutions or dispersions may be contained in any suitable vessel, such as a vial or a syringe barrel.

In some embodiments, the kit comprises at least one hydrogel precursor having a polymer terminated with an aminooxy group in the form of a dried powder and at least one hydrogel precursor having a polymer terminated with a reactive oxo group in the form of a dried powder. The powders may be contained in separate containers or they may be premixed and contained in a single container. The kit may also comprise a buffer solution for hydrating the powders.

C. EXAMPLES

In some embodiments, a new approach is provided to prevent postsurgical cardiac adhesions using rapidly forming biocompatible polymer hydrogels (e.g. poly(ethylene glycol) (PEG) and/or poly(vinyl alcohol) polymers or copolymers) cross-linked by oxime bonds that form a protective layer over the epicardium. Oxime bond formation is the Schiff base reaction between an aminooxy group (e.g. hydroxyl amine, alkoxyl amine, etc.) and a reactive oxo group (e.g. ketone, aldehyde, etc.), and is used to both cross-link polymers and attach the hydrogel to free amines on the tissue. In some embodiments, the oxime bonds bind to tissue in vivo. The hydrogels, and methods of use thereof, are suitable for preventing or resisting tissue or cell adhesions or protein adsorption.

In some embodiments, a two component polymeric system is provided that can be easily sprayed, dripped, and/or painted directly onto the heart forming an anti-adhesion layer within seconds to minutes. With this system the degree of swelling and degradation time can be controlled yet not interfere with cardiac function. Since the oxime bond is dynamic, the material can also be easily removed if necessary by addition of free aminooxy groups (e.g. hydroxyl amines, alkoxyl amines, etc.) or reactive oxo groups (e.g. ketones, aldehydes, etc.).

In some embodiments, the invention provides hydrogels, and methods of use thereof, for preventing or resisting tissue or cell adhesion and/or protein adsorption. In some embodiments, oxime cross-linking chemistry of poly(ethylene glycol) (PEG) was applied to star polymers. Electron deficient aldehyde is capable of reacting with amines on the tissue surface as well as with hydroxylamines to rapidly form a PEG-hydrogel on cardiac tissue (see FIG. 1). This material has the ability to have tunable gelation kinetics, inhibit cellular adhesion, and is capable of adhering to different cardiac tissues for over two weeks.

Figure 2:
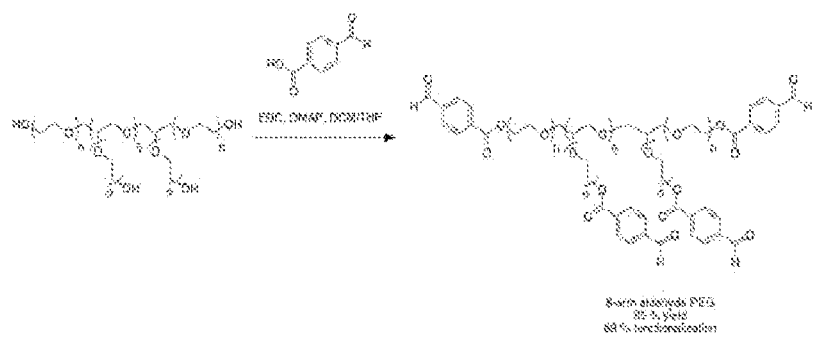
FIG. 2. Synthesis of 8-arm aldehyde PEG.
Figure 3:
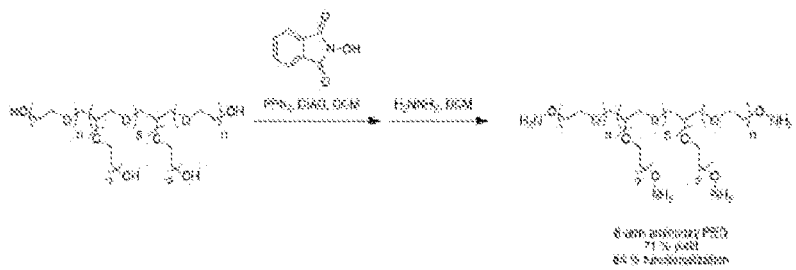
FIG. 3. Synthesis of 8-arm aminooxy PEG.

In some embodiments, materials synthesized via oxime chemistry were used because, since the equilibrium lies far toward the oxime product, these bonds exhibit excellent aqueous stability over imines and hydrazones. Previous work showed this chemistry to form hydrogels for catheter delivery using a 4-arm PEG (20,000 g/mole) esterified with levulinic acid and a 4-arm hydroxylamine PEG (20,000 g/mole). At physiological pH and temperature the 4-arm system exhibited very slow gelation (>2 days).[15] To increase the gelation rate, the electrophilicity of the carbonyl group was increased while a hydrolysable ester was maintained. An 8-arm star PEG (10,000 g/mole and/or 5,000 g/mole) were esterified with 4-carboxylbenzaldehyde (ald-PEG) (see FIG. 2). The 8-arm aminoxy-PEG (AO-PEG) with the 8-arm star PEG (10,000 g/mole and/or 5,000 g/mole) were synthesized via Mitsunobu with N-hydroxyphthalimide followed by deprotection with hydrazine (see FIG. 3).[14, 15]

Figure 4:
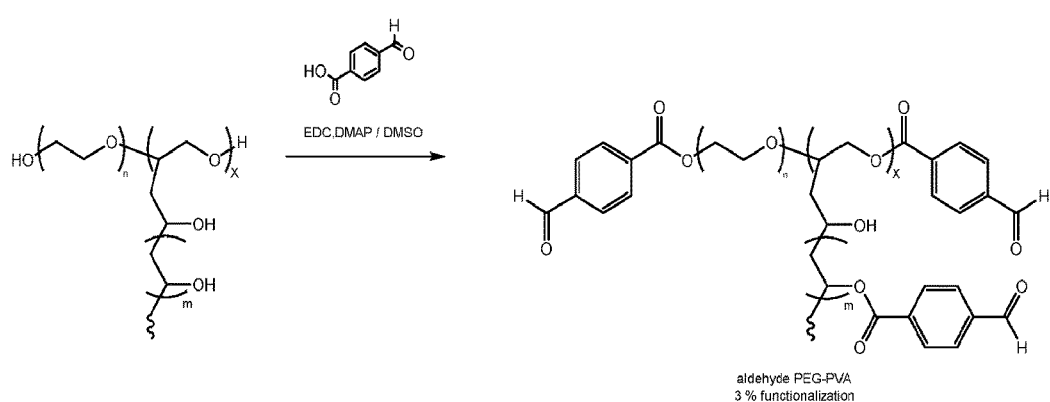
FIG. 4. Synthesis of aldehyde PEG-PVA.

In some embodiments, a PEG-PVA (45,000 g/mole) was esterified with 4-carboxylbenzaldehyde (ald-PEG-PVA) (see FIG. 4). More particularly, PEG-PVA (Kollicoat IR) (3.0 g, 0.066 mmol) was dissolved in anhydrous dimethylsulfoxide (60 mL), followed by addition of 4-carboxybenzaldehyde (1.080 g, 7.2 mmol). The reaction flask was placed into an ice bath followed by addition of N-(3-dimethylaminopropyl)-N'-ethylcarbodiimide hydrochloride (1.380 g, 7.2 mmol) and 4-(dimethylamino)pyridine (39.0 mg, 0.3 mmol). After 48 h methanol (1.5 mL) was added and stirred for 3 h. The crude reaction product was then dialyzed (molecular weight cut off 3,500 g/mole) against methanol to afford the aldehyde PEG-PVA (ald-PEG-PVA) in 3.0% functionalization.

Figure 5:
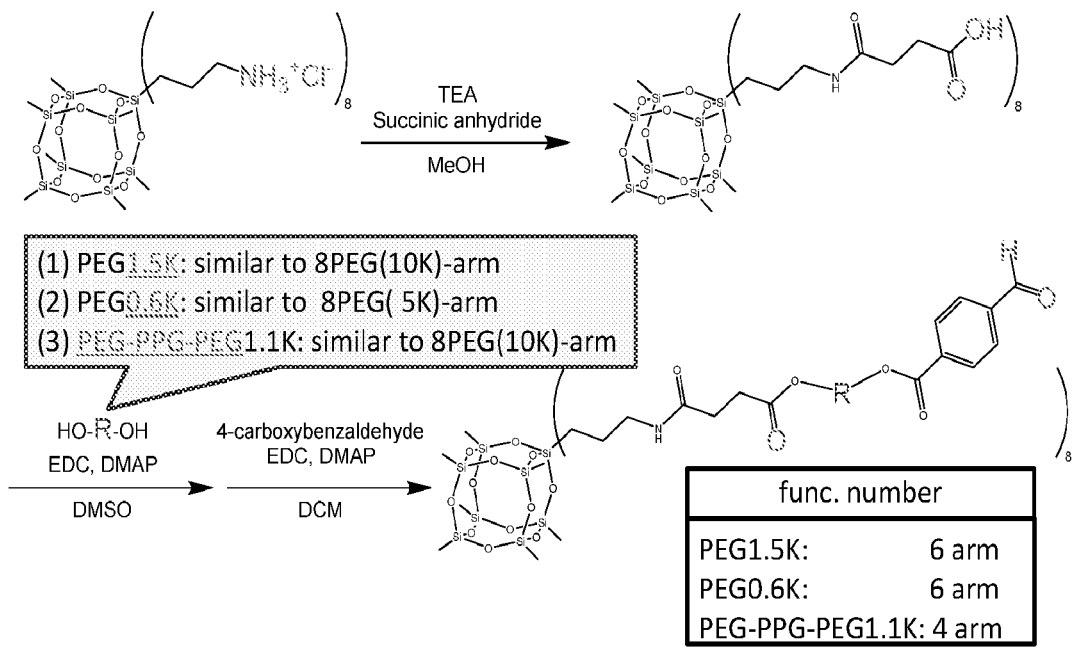
FIG. 5. Synthesis of 8-arm aldehyde POSS PEG.

In some embodiments, (3-Aminopropyl)triethoxysilane (200 mL, 0.86 mol) and concencntrated hydrochloric acid (35-37%, 270 mL) in methanol (1,600 mL) produced 8POSS-$NH_3^+$ as a white precipitate after 4 days at room temperature. The product was obtained after filtration, washing with cold methanol, and drying. 8POSS-$NH_3^+$ was spectroscopically pure as a white solid. Succinic anhydride (80.00 g, 0.80 mol) was added to a solution of 8POSS-$NH_3^+$ (21.46 g, 18.39 mmol) and triethylamine (TEA) (20 mL, 0.14 mol) in methanol (1,000 mL), and the reaction mixture was stirred at room temperature for 30 minutes. Chloroform (2,000 mL) was poured into the reaction solution, and the white precipitation was collected via filtration and washed with chloroform and tetrahydrofuran (THF). Subsequently, the product was resolved in 60 mL of formic acid and reprecipitated by the addition of 1000 mL water. The white precipitation was filtered and washed with water until filtrate indicated pH 7. 8POSS-COOH was obtained as a white solid. 8POSS-COOH (3.00 g, 1.78 mmol) and alcohol-terminated PEG (PEG Mn ca. 1.5 k) (124.12 g, 85.61 mmol) were dissolved in anhydrous dimethyl sulfoxide (200 mL). The reaction flask was placed into an ice bath followed by addition of N-(3-dimethylaminopropyl)-N'-ethylcarbodiimide hydrochloride (EDC) (16.41 g, 85.61 mmol) and 4-(dimethylamino)pyridine (DMAP) (0.44 g, 3.57 mmol). After 48 h methanol (10 mL) was added and stirred for 3 h. The crude reaction product was then dialyzed (MW cut off 3,500 g/mol) against methanol to afford the 8POSS-PEG10 k (8.76 g) in 90.69% functionalization (see FIG. 5).

Figure 6:
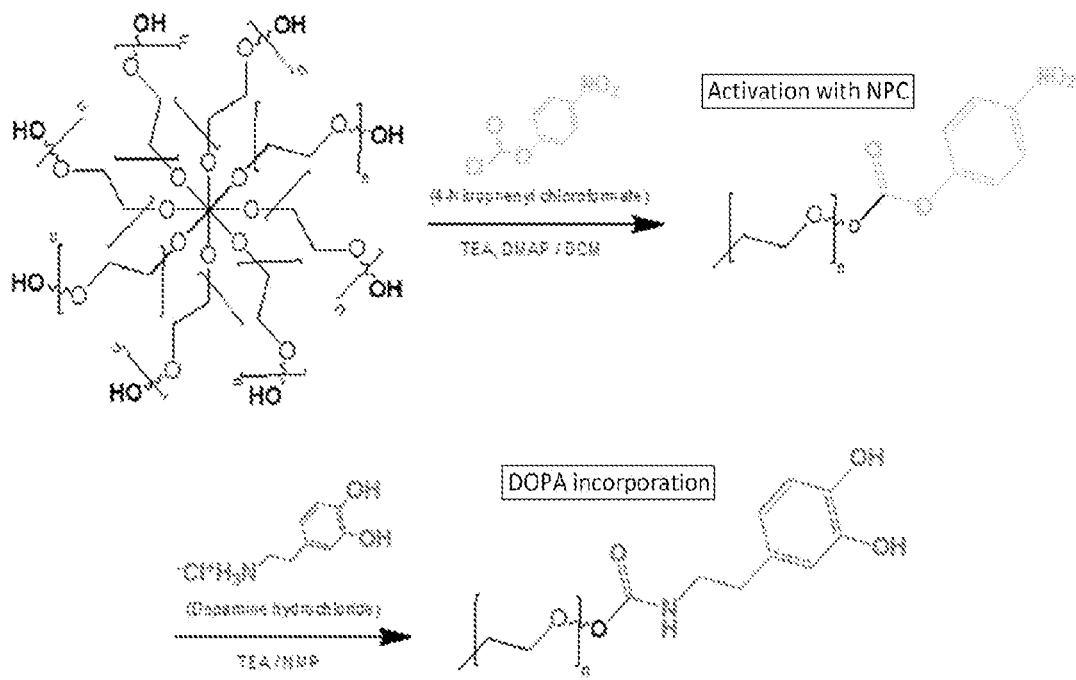
FIG. 6. Synthesis of 8-arm catechol PEG.

In some embodiments, 8-arm PEG (PEG MW ca. 1.3 k) (5.00 g, 0.50 mmol) was dissolved in anhydrous dichloromethane (DCM) (100 mL). The reaction flask was placed into an ice bath followed by addition of 4-nitrophenyl chloroformate (NPC) (8.06 g, 40.00 mmol), triethylamine (TEA) (5.58 mL, 40.00 mmol) and DMAP (0.81 g, 4.00 mmol). After 3 h the reaction solution was poured into cold diethyl ether (900 mL), and the orange precipitation was collected via filtration and washed with cold diethyl ether. NPC-activated 8PEG10k was obtained as a yellow solid (see FIG. 6).

$^1$H NMR (data not shown) was used to confirm the successful synthesis and the functionalization ratio of each PEG component. The average number of functionalized arms were calculated and are reported in FIG. 7.

Figure 9B:
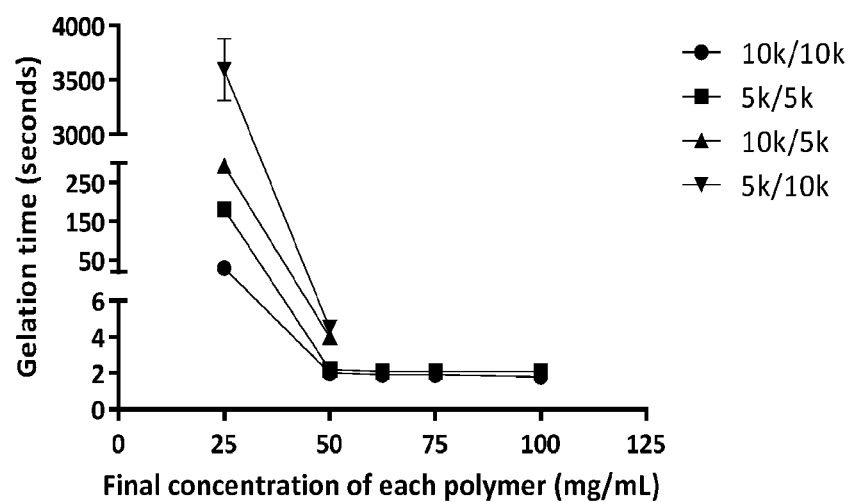
Figure 10A:
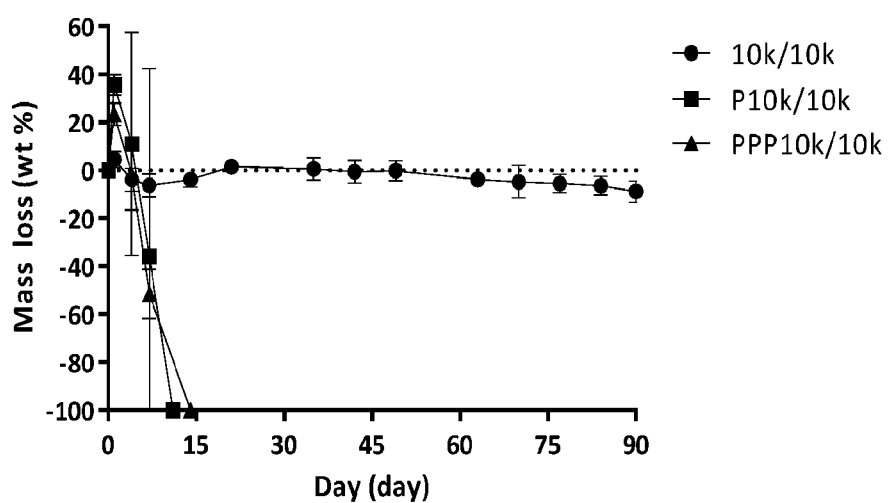
FIGS. 10A-10D.
Figure 10B:
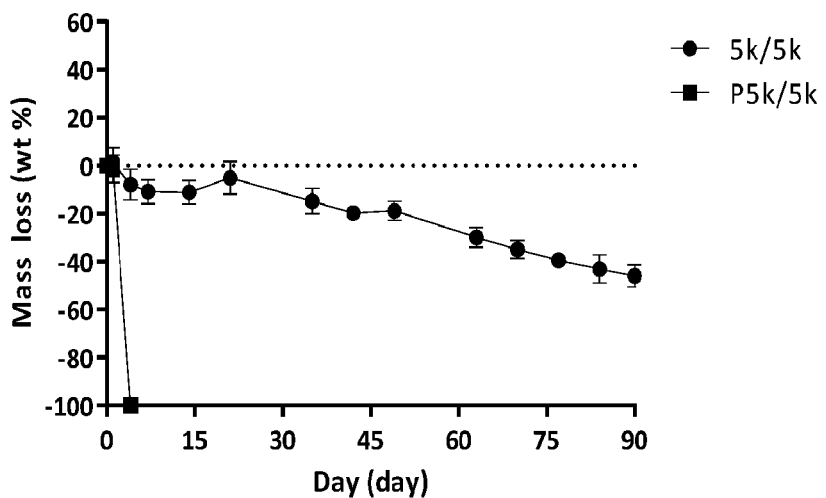
Figure 10C:
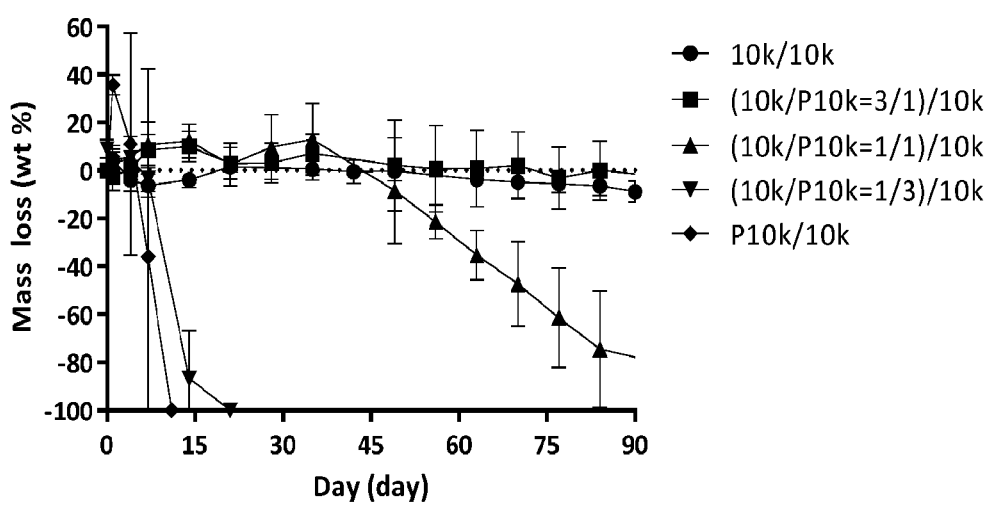
Figure 10D:
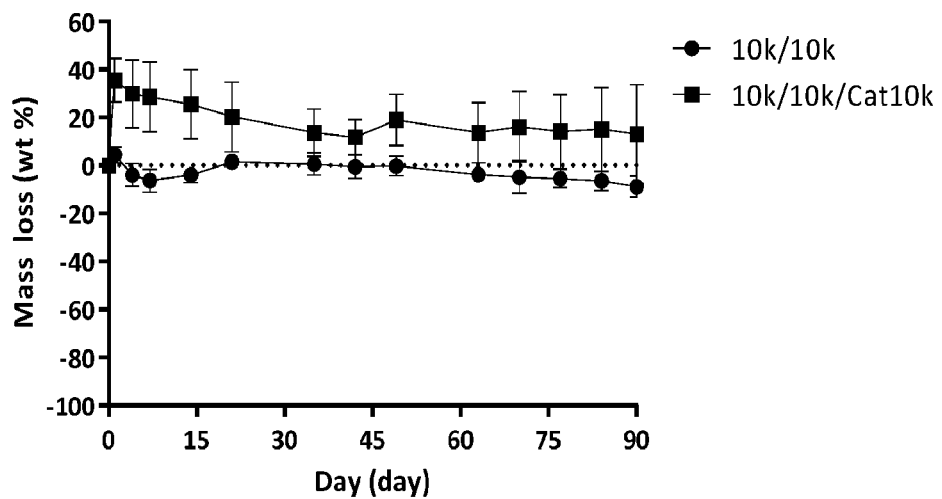

In some embodiments, a hydrogel system is provided that was modified by increasing the number of cross-linking sites from four to eight and decreasing the molecular weight to 10,000 g/mole and/or 5,000 g/mole. These modifications increased the weight percent of functional groups, increased the gelation rate, and formed a cross-linked network with minimal swelling. Upon mixing the ald-PEG (10,000 g/mole) and AO-PEG (10,000 g/mole) in deionized water at 25° C. at equal concentrations, transparent hydrogels were rapidly formed (see FIG. 9A). Exemplary tested hydrogels are reported in FIG. 8. The gelation rate was tunable based upon the weight percent of material from 3600 seconds to <2 seconds (see FIG. 9B).

For in vivo applications, the hydrogel is preferably hydrolytically stable for at least two weeks at physiological conditions. The percent mass loss over time was characterized for hydrogel formulations (see FIGS. 10A-10D) that were incubated in 4× the gel volume of PBS, which was changed daily.

Figure 11:
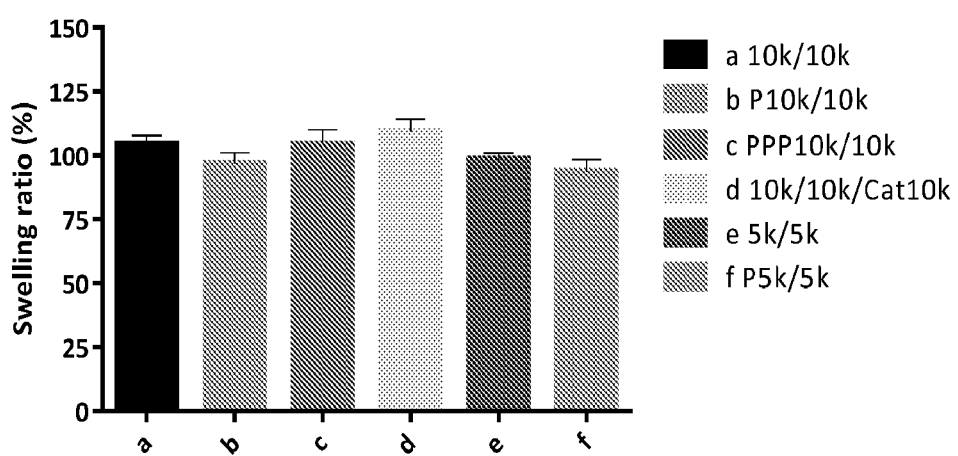
FIG. 11. Swelling ratio of hydrogels.

The 62.5 to 100 mg/mL formulation in final concentration of hydrogels were further characterized since the gelation time was the most rapid for this system. First swelling ration of hydrogels were measured (see FIG. 11).

Figure 12:
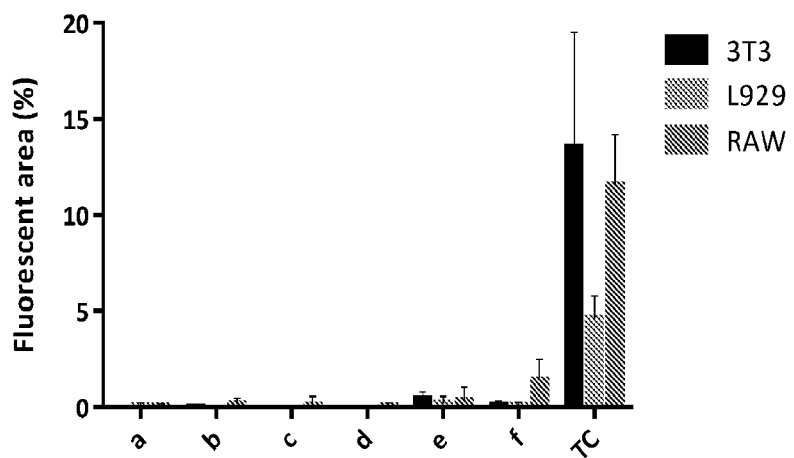
FIG. 12. Percent area of fluorescence of membrane labeled 3T3 fibroblasts, L929 figroblasts and RAW macrophages 24 h after seeding (functional group ratio is aldehyde:aminooxy and TC is tissue culture plastic).

Since functional group ratio affected gel stability it was further tested if an excess of either functional group would change the ability of cells to adhere to the material. The hydrogels were formed and swelled at 37° C. for 24 h. Then 3T3 fibroblasts, L929 fibroblasts or RAW macrophages, in which the membrane was fluorescently labeled, were seeded on top of the hydrogels or non-coated tissue culture plastic (TC). These cell types were chosen since they are cell types that infiltrate biomaterials in vivo. The cell volume was optimized to ensure that a monolayer was formed after seeding onto tissue culture plastic (TC), which acted as the positive control. After 24 h, the percent area fluorescence was quantified (see FIG. 12). Both the 3T3, L929 fibroblasts and the macrophages exhibited less than 2% fluorescent area for all three functional group ratios of the hydrogels (1:1, 1:3, and 3:1 of ald-PEG:AO-PEG), while TC plastic was between 4.5-14% fluorescent area for all tested cell types. This demonstrated that an excessive amount of either functional group and the oxime bond did not alter the anti-cellular adhesive properties of PEG hydrogels.

Cellular adhesion was observed with the different gel formulations, and it was examined if the elution products exhibited any cytotoxicity by two different methods. First, an agar elution assay was used. A monolayer of cytosol labeled L929 fibroblasts was formed and agar gel containing serum free media was formed over the monolayer. After the cells had been serum starved for 24 h, the three different 100 mg/mL hydrogels (1:1, 1:3, and 3:1 of ald-PEG:AO-PEG) were placed on top of the agar gel and cultured for an additional 24 h. The negative control was a piece of latex and the positive control was a piece of sterile filter paper soaked in serum free media. From bright field images of cells directly beneath the substrates it was observed that there is a distinct difference in cell morphology between the latex and filter paper groups.

Figure 13:
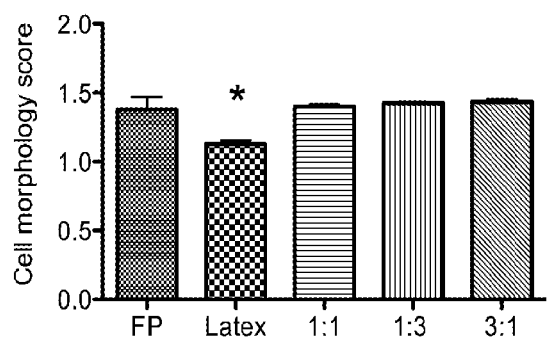
FIG. 13. Results of cytocompatability assay showing fibroblast morphology scores for sterile filter paper soaked in serum free media (positive control), a piece of latex (negative control), and 100 mg/mL hydrogels (1:1, 1:3, and 3:1 of ald-PEG-AO-PEG).
Figure 16A:
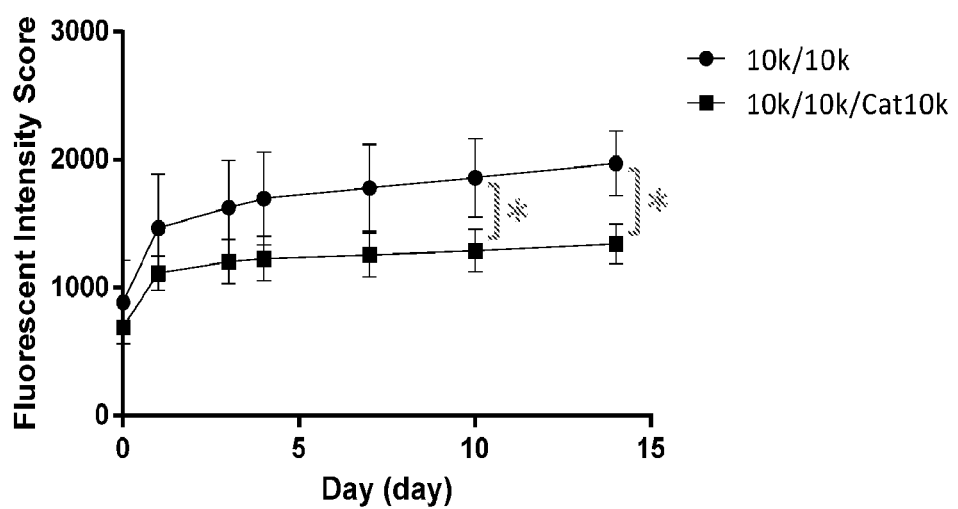
FIGS. 16A-16D. Release amount of hydrogels from tissue surface after two weeks (functional group ratio is aldehyde: amino-oxy). Tissue sections.
Figure 16B:
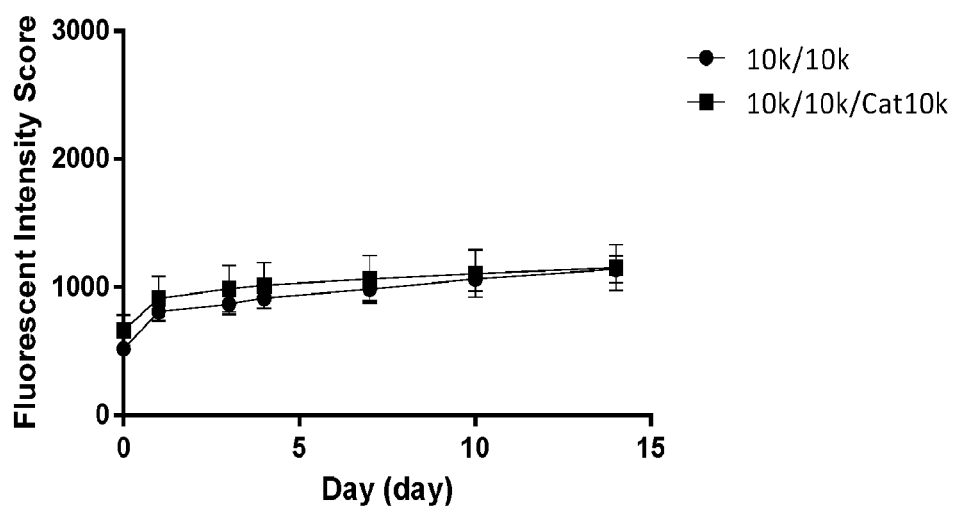
Figure 16C:
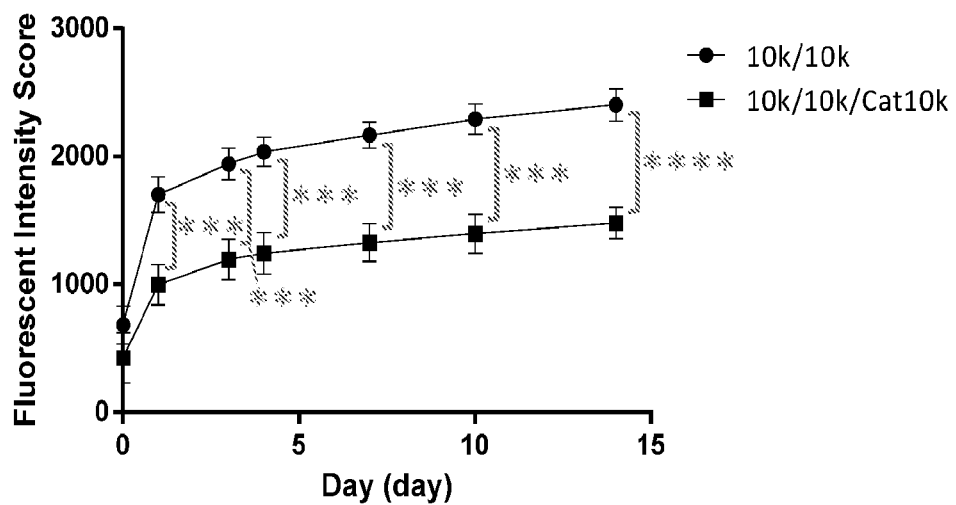
Figure 16D:
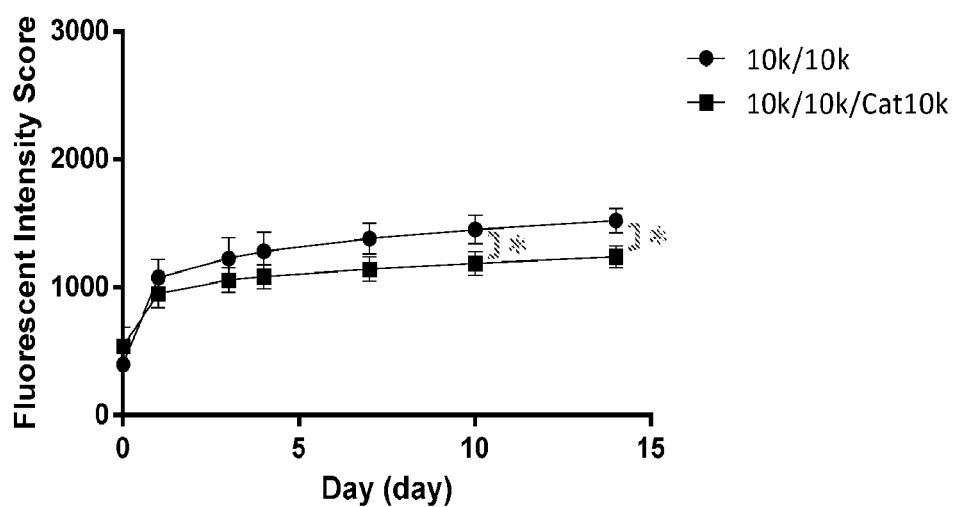

Cells were then scored based upon morphology from 1 to 3. A score of 1 was a rounded cell where the long and short axes were of equal length. A score of 3 was a spread-out cell with multiple protrusions where the long axis was >2 times longer than the short axis. The fibroblasts directly beneath the latex exhibited more rounded morphologies as indicated by the morphology score (see FIG. 13). Fibroblasts directly beneath the hydrogel formulations had similar cell morphology scores to the healthy cells beneath the non-toxic filter paper (see FIG. 13). The lower morphology score for the latex group is indicative of toxic elution products, while the score for the hydrogel groups is similar to the filter paper group.

The second cytocompatibilty assay was performed on the elution product using a doped-media assay. A monolayer of 3T3 fibroblasts was serum starved for 24 h. Then the cells were cultured with serum free media doped with different concentrations of elution products from the different hydrogel formulations for 24 h, and the metabolic activity of the cells were measured using Alamar Blue. While all of the 3:1 ald-PEG:AO-PEG doped groups trend lower than the PBS, 1:1, and 1:3 groups show no statistical difference between any of the doped media groups (see FIGS. 14A-C) when compared to media doped with the same amount of PBS, indicating there is no effect on metabolic activity. This result combined with the agar elution assay indicate that the elution products of the 1:1, 1:3, and 3:1 ald-PEG:AO-PEG 100 mg/mL hydrogels are cytocompatible.

The ability to adhere to different cardiac tissue ex vivo was examined A sodium periodate oxidized dextran/PEG-amine system has been shown to exhibit different adhesion times to different tissues.[16] It was tested if this occurred with oxime cross-linked gels and if excess functional groups altered retention time on different cardiac tissues. Both PEG components were fluorescently labeled. Hydrogels were formed on aorta, adipose, atrium and ventricle (see FIG. 15). The elutions from the gels coated tissues were compared to the same volume of gels formed on tissue culture plastic. The PBS was replaced after 1 h, 4 h, 8 h, and then every 24 h for two weeks.

For all tissues, a burst release of hydrogel was observed within the first 12 h. However after 2 days, significantly less flourescently labeled polymer was released. This pattern was observed for 15 days. For all tissues except adipose, hydrogels including a polymer comprising catechol groups showed higher retention on the heart over two weeks (see FIG. 16A-16D).

In some embodiments a fast-gelling oxime cross-linked poly(ethylene glycol) (PEG) and/or poly(vinyl alcohol) hydrogel system is provided. The gelation rate and degradation are tunable based upon the weight percent of the polymers. In some embodiments, the gelation rate and degradation rate are tunable based upon the weight percent of the 8-arm aldehyde-PEG and aminooxy-PEG. The 100 mg/mL formulations gel in less than 2 seconds. Variation of the functional group ratio from 1:1, 1:3, and 3:1 ald-PEG:AO-PEG prevent adhesion of fibroblasts and macrophages, and the elution products are cytocompatible. In some embodiments, the cardiac tissue type and the functional group ratio of aldehyde:aminooxy directly impacted the ability of the material to adhere to the different cardiac tissue surfaces. In some embodiments, the type of tissue and functional group ratio effect the rate of gel degradation. In some embodiments, the types of tissue as well as the composition of the gels used to coat the tissue directly impact the retention of the material over time, which has important implications when designing materials for clinical translation.

In some embodiments, the rapid gelling hydrogel for preventing surgical adhesions is a unique system in three aspects: 1) the hydrogel is composed of polymers such as poly(ethylene glycol) (PEG) and/or poly(vinyl alcohol) polymers or copolymers, for example multi-armed PEG components (e.g. PEG-aminooxy and PEG-aldehyde/ketone), that rapidly react to form a hydrogel that can coat tissue surfaces. The formation time of this hydrogel can be tuned from seconds to minutes by polymer concentration or pH of the formulation. This is unique since the three main prior art systems consist of a) thermo-responsive material of hyaluronic acid/cellulose, b) fibrin glue, and c) PEG-NHS+ PEG amine/oligo-lysines. The PEG-NHS systems all gel rapidly however, this gelation only occurs over a narrow pH window (pH 7.5-9). In certain embodiments, the oxime cross-linked hydrogels and/or polymer precursors are injectable with a tunable gelation rate of seconds to minutes over a broad range of concentrations (20 mg/mL to 100 mg/mL) and pHs (4-10). This tunability is due to the oxime cross-linking reaction. Furthermore the reactive oxo group (e.g. aldehyde/ketone) component also facilitates adhesion to the tissue surface by reaction with native amines to form imines Additionally, in some embodiments, the oxime cross-linked hydrogels contain hydrolysable ester linkages that can be manipulated to tune the rate of hydrolysis of the material post-gelation; 2) once formed the hydrogel system has very minimal swelling ratio (112%). This is important for application on the heart since material swelling can disrupt the natural function of the organ. This is in direct contrast to the PEG-NHS+amine systems that exhibit a very high swelling ratio from 200-600% of the initial volume; and 3) since the presently disclosed hydrogels are cross-linked via oxime bonds the cross-linking can also be reversed with addition of free aminooxy groups (e.g. hydroxyl amines and alkoxy amines) or free reactive oxo groups (e.g. ketones/aldehydes).

Figure 17A:
FIG. 17A depicts the surface coated with a RO-AO-catechol hydrogel.
Figure 17B:
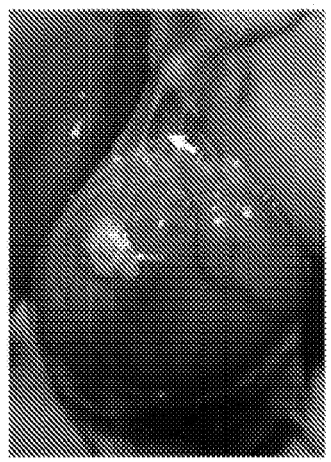
FIG. 17B depicts the untreated control.
Figures 18A, 18B:
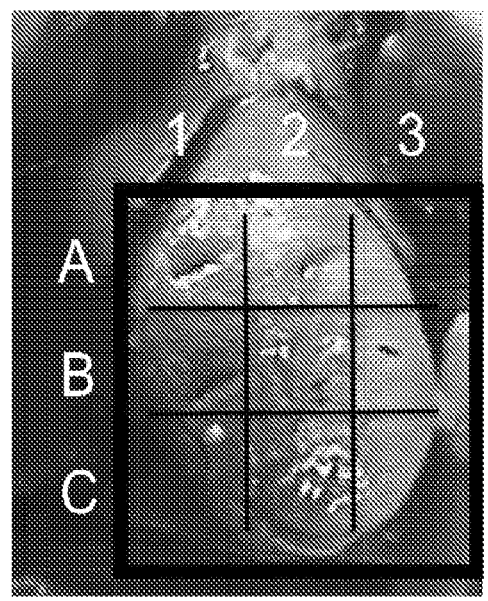
FIGS. 18A-18B. Division of epicardial area for macroscopic adhesion (FIG. 18A) and grading scale of adhesion severity and explanation of physiological characteristics (FIG. 18B).

An in vivo rat cardiac adhesion model was used to test the anti-adhesion properties of the Ald-AO-DOPA hydrogel (consisting of 100 mg/mL Ald-PEG and AO-PEG and 75 mg/mL DOPA-PEG, corresponding to a Ald:AO:DOPA ratio of 1:1:0.75) compared to the Ald-AO hydrogel (consisting of 100 mg/mL Ald-PEG and AO-PEG corresponding to a Ald:AO ratio of 1:1) and untreated rats. Gross assessment of cardiac adhesion formation was preformed when the chest was re-entered. Before dissecting the adhesions to harvest the heart, images were taken and given to blinded graders for assigning adhesion scores. The heart was divided into 9 segments, and each segment was given an overall adhesion score based on the presence and severity of adhesions from 0-4 (FIGS. 18 A and 18B). The average score over these 9 segments was reported as the average adhesion score. The average adhesion intensity was calculated over all regions that showed adhesion formation. The maximum adhesion intensity score was also reported for each animal. Representative images of the observed adhesions in Ald-AO-DOPA and control groups are shown in FIGS. 17A and 17B, respectively.

Figure 19A:
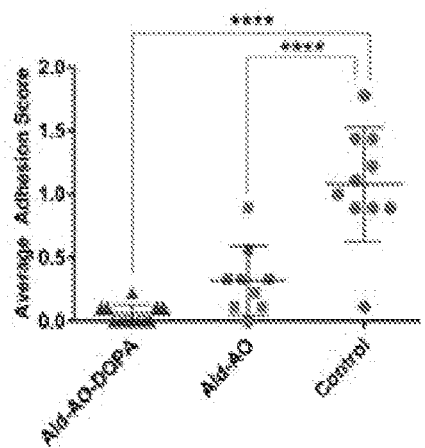
FIGS. 19A-19C. Average adhesion scoring (FIG. 19A), average intensity scoring (FIG. 19B), and maximum intensity scoring (FIG. 19C) after two weeks in a rat model.
Figure 19B:
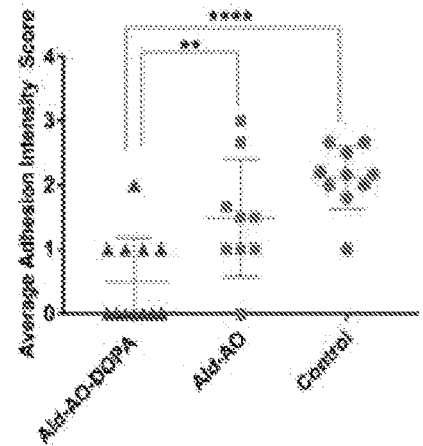
Figure 19C:
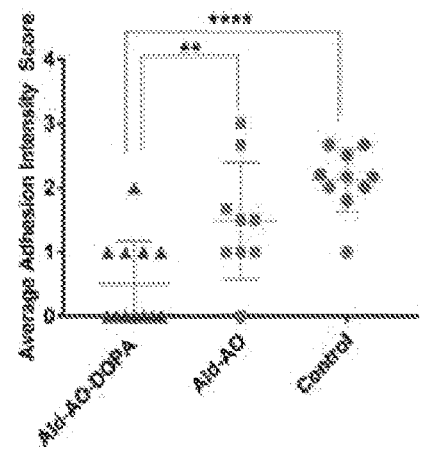

At 2 weeks, there was a significant reduction in average adhesion score when Ald-AO-DOPA and Ald-AO were applied, compared to the untreated control (FIGS. 19A-19C). All of the treatment groups consistently received low adhesion scores, however Ald-AO-DOPA (0.06±0.07) and Ald-AO (0.32±0.27) groups were significantly lower compared to the untreated (1.08±0.45) control at 2 weeks (FIG. 19A). The average intensity scores of the adhesions showed similar results, with a significantly reduced adhesion intensity score when Ald-AO-DOPA (0.50±0.67) was applied, compare to Ald-AO (1.48±0.91) and the untreated control (2.12±0.49) (FIG. 19B). There was no difference in average adhesion intensity score reported for Ald-AO and untreated groups. Maximum adhesion intensity score was the final parameter used to grade adhesion formation and hydrogel efficacy. Compared to Ald-AO (1.67±1.0) and untreated groups (2.60±0.69), Ald-AO-DOPA (0.50±0.67) application resulted in significantly lower maximum adhesion intensity (FIG. 19C).

Figure 20A:
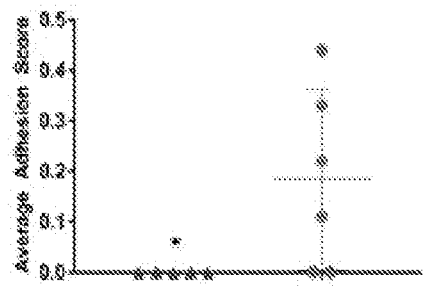
FIGS. 20A-20G. Adhesion formation and heart function assessed for administration of Ald-AO-DOPA and the untreated control. Average adhesion scoring (FIG. 20A), average intensity scoring (FIG. 20B), and maximum intensity scoring (FIG. 20C) after 4 weeks. M-mode echocardiograph (FIG. 20D), fraction shortening (FIG. 20E), left ventricular internal diameter diastole ($LVID_D$) (FIG. 20F), and left ventricular internal diameter systole (LVIDs) (FIG. 20G) assessed 3±1 days post hydrogel application using M-mode echocardiography.
Figure 20B:
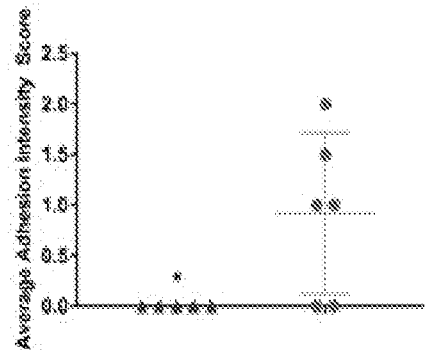
Figure 20C:
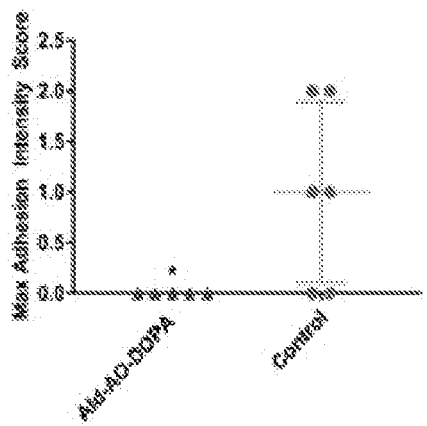
Figure 20D:
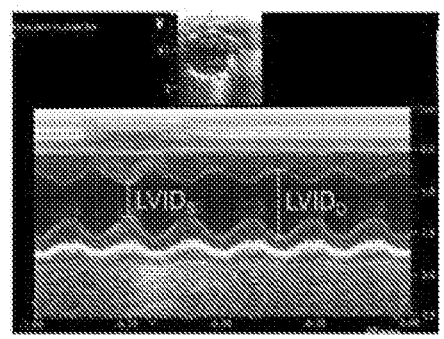
Figure 20E:
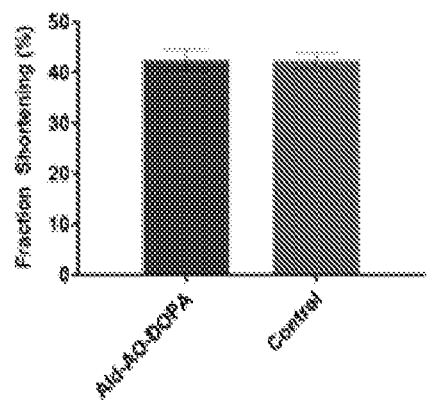
Figure 20F:
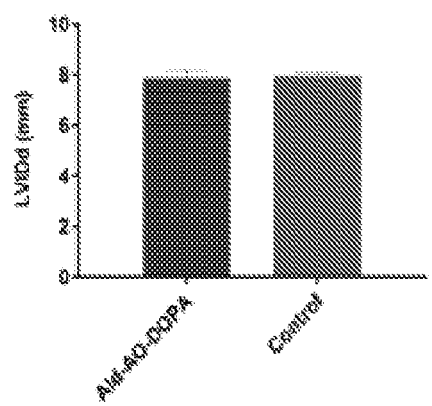
Figure 20G:
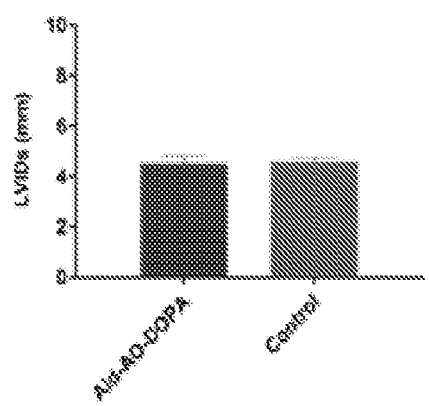

Adhesion formation and cardiac function were assessed in an in vivo study, comparing untreated rats to Ald-AO-DOPA. At 4 weeks, a reduction in adhesion formation and severity was observed (FIG. 20). All of the rats treated with Ald-AO-DOPA showed no signs of adhesion formation and received an overall adhesion score of 0, which was significantly lower than the untreated group (0.18±0.18) (FIG. 20A). Consistent with 2 week results, the average adhesion intensity score (FIG. 20B) and maximum adhesion intensity score (FIG. 20C) for Ald-AO-DOPA (scores of 0 for both measurements) were also significantly lower than the untreated group (average adhesion intensity 0.92±0.80, maximum adhesion intensity 1.00±0.89).

To ensure the hydrogels did not impede cardiac function, M-mode echocardiography was conducted 3±1 days post hydrogel application (FIGS. 20D-G). When Ald-AO-DOPA was applied there was no difference in end-diastolic left ventricular internal diameter ($LVID_D$), end-systolic left ventricular internal diameter (LVIDs), or fractional shortening (FS) compared to the untreated group, indicating normal cardiac function following gel application.

Figure 21:
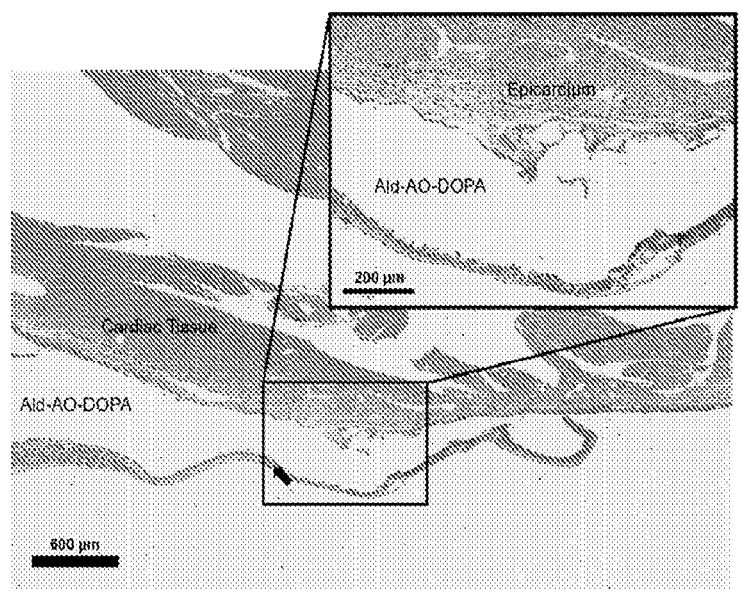
FIG. 21. Hematoxylin and Eosin Y (H&E) staining of Ald-AO-DOPA tissue samples to verify biocompatibility of the oxime hydrogel systems.

Histological assessment of chronic inflammation was performed by a trained histopathologist on hearts that were harvested at 4 weeks. Hematoxylin and Eosin Y (H&E) staining revealed the presence of Ald-AO-DOPA hydrogel fragments on the epicardium at 4 weeks, indicating that only partial degradation had occurred. Minimal macrophage infiltration (green arrow) is visible at high magnification (FIG. 21). A thin fibrotic capsule forming around Ald-AO-DOPA (~50 µm) (black arrow) could be observed, however, there was no indication of lymphocyte and neutrophil infiltration, suggesting that no chronic inflammation was occurring (FIG. 21).

Modifications and variations of the methods and hydrogels described herein will be obvious to those skilled in the art from the foregoing detailed description. Such modifications and variations are intended to come within the scope of the appended claims.

REFERENCES

1. Bouten P J M, Zonjee M, Bender J, Yauw S T K, van Goor H, van Hest J C M, Hoogenboom R. The chemistry of tissue adhesive materials. *Prog Polym Sci.* 2014; 39:1375-1405.
2. Spotnitz W D. Hemostats, sealants, and adhesives: A practical guide for the surgeon. *Am Surgeon.* 2012; 78:1305-1321.
3. Cannata A, Petrella D, Russo C F, Bruschi G, Fratto P, Gambacorta M, Martinelli L. Postsurgical intrapericardial adhesions: Mechanisms of formation and prevention. *Ann Thorac Surg.* 2013; 95:1818-1826.
4. Liakakos T, Thomakos N, Fine P M, Dervenis C, Young R L. Peritoneal adhesions: Etiology, pathophysiology, and clinical significance—recent advances in prevention and management. *Digest Surg.* 2001; 18:260-273.
5. Yeo Y, Kohane D S. Polymers in the prevention of peritoneal adhesions. *Eur J Pharm Biopharm.* 2008; 68:57-66.
6. Nkere U U. Postoperative adhesion formation and the use of adhesion preventing techniques in cardiac and general surgery. *Asaio J.* 2000; 46:654-656.
7. Salminen J T, Mattila I P, Puntila J T, Sairanen H I. Prevention of postoperative pericardial adhesions in children with hypoplastic left heart syndrome. *Interact Cardiov Th.* 2011; 12:270-272.
8. Morales D, Williams E, John R. Is resternotomy in cardiac surgery still a problem? *Interact Cardiov Th.* 2010; 11:277-286.
9. Bel A, Ricci M, Piquet J, Bruneval P, Perier M C, Gagnieu C, Fabiani J N, Menasche P. Prevention of postcardiopulmonary bypass pericardial adhesions by a new resorbable collagen membrane. *Interact Cardiov Th.* 2012; 14:469-473.
10. Leggat P A, Smith D R, Kedjarune U. Surgical applications of cyanoacrylate adhesives: A review of toxicity. *Anz J Surg.* 2007; 77:209-213.
11. Ulrich S, Boturyn D, Marra A, Renaudet O, Dumy P. Oxime ligation: A chemoselective click-type reaction for accessing multifunctional biomolecular constructs. *Chem-Eur J.* 2014; 20:34-41.
12. Ostuni E, Chapman R G, Holmlin R E, Takayama S, Whitesides G M. A survey of structure-property relationships of surfaces that resist the adsorption of protein. *Langmuir.* 2001; 17:5605-5620.
13. Zhang M Q, Desai T, Ferrari M. Proteins and cells on peg immobilized silicon surfaces. *Biomaterials.* 1998; 19:953-960.
14. Grover G N, Lam J, Nguyen T H, Segura T, Maynard H D. Biocompatible hydrogels by oxime click chemistry. *Biomacromolecules.* 2012; 13:3013-3017.
15. Grover G N, Braden R L, Christman K L. Oxime cross-linked injectable hydrogels for catheter delivery. *Adv Mater.* 2013; 25:2937-2942.
16. Artzi N, Shazly T, Baker A B, Bon A, Edelman E R. Aldehyde-amine chemistry enables modulated biosealants with tissue-specific adhesion. *Adv Mater.* 2009; 21:3399.

What is claimed is:

1. An oxime cross-linked biocompatible hydrogel comprising:
a first polymer comprising an aminooxy group selected from a hydroxyl amine and an alkoxy amine polymerized to a second polymer comprising a reactive oxo group, and a third polymer comprising a catechol group, wherein the hydrogel has a surface comprising a surface oxo group that reversibly binds an amine group on a living tissue surface to form an imine, and wherein the weight ratio of first polymer:second polymer:third polymer is 1:1:0.75-1.

2. The hydrogel of claim 1, wherein the reactive oxo group and the surface oxo group are ketones.

3. The hydrogel of claim 1, wherein the reactive oxo group and the surface oxo group are aldehydes.

4. The hydrogel of claim 1, wherein the aminooxy group is a hydroxyl amine.

5. The hydrogel of claim 1, wherein the aminooxy group is an alkoxy amine.

6. The hydrogel of claim 1, wherein the catechol group is dopamine.

7. The hydrogel of claim 1, wherein the weight ratio of first polymer:second polymer:third polymer is 1:1:0.75.

8. The hydrogel of claim 1, wherein the first polymer and the second polymer are each selected from the group consisting of poly(ethylene glycol), multi-arm poly(ethylene glycol), copolymer of poly(ethylene glycol) and poly(propylene glycol), multi-arm copolymer of poly(ethylene glycol) and poly(propylene glycol), hyaluronic acid, alginate, dextran, carboxymethylcellulose, cellulose, poly(vinyl alcohol), or combinations thereof.

9. The hydrogel of claim 1, wherein the first polymer comprises eight-armed aminooxy poly(ethylene glycol) and the second polymer comprises eight-armed oxo poly(ethylene glycol).

10. The hydrogel of claim 1, wherein the first polymer comprises eight-armed aminooxy poly(ethylene glycol) and the second polymer comprises aldehyde poly(ethylene glycol)-poly(vinyl alcohol).

11. The hydrogel of claim 1, wherein the third polymer comprises an eight-armed catechol poly(ethylene glycol).

12. The hydrogel of claim 1, wherein the hydrogel comprises approximately between 25 and 200 mg/mL of the first polymer and the second polymer in final concentration of hydrogels.

13. The hydrogel of claim 1, wherein the hydrogel has a storage modulus of about less than 20 kPa.

14. The hydrogel of claim 1, wherein the hydrogel has a swelling ratio of less than about 130%.

15. The hydrogel of claim 1, further comprising a bioactive agent.

16. A method of administering an oxime cross-linked bioadhesive hydrogel to a tissue for use as an in-situ anti-adhesion barrier comprising:
    administering to a living tissue of an individual an effective amount of a combination of a first polymer comprising an aminooxy group selected from a hydroxyl amine and an alkoxy amine, a second polymer comprising a reactive oxo group, and a third polymer comprising a catechol group, wherein the weight ratio of first polymer:second polymer:third polymer is 1:1:0.75-1,
    wherein the first polymer and second polymer are initially mixed and react to form an oxime cross-linked biocompatible hydrogel proximate to the tissue,
    wherein the hydrogel has a surface comprising a surface oxo group, and
    wherein the surface oxo group reversibly binds a surface amine on the tissue to form an imine.

17. The method of claim 16, wherein the tissue is cardiac tissue.

18. The method of claim 16, wherein the oxime cross-linked biocompatible hydrogel is formed in about 5 minutes or less.

19. The method of claim 16, wherein the combination of the first polymer, the second polymer and the third polymer is administered by spraying, dripping, or painting the first polymer, the second and the third polymer directly onto the tissue.

20. The method of claim 16, wherein the hydrogel is capable of adhering to the tissue for about two or more weeks.

21. The method of claim 16, wherein the hydrogel reduces cellular adhesion and protein adsorption to the tissue.

22. The method of claim 16, further comprising reversing hydrogel cross-linking by administering a free aminooxy group selected from a hydroxyl amine and an alkoxy amine, or a reactive oxo group.

23. A kit for making an oxime-linked bioadhesive hydrogel for use as an in-situ anti-adhesion tissue barrier comprising;
    a. a first polymer comprising an aminooxy group;
    b. a second polymer comprising a reactive oxo group;
    c. a third polymer comprising a catechol group; and
    d. instructions for combining the first, second, and third polymers to form the bioadhesive hydrogel, wherein the weight ratio of first polymer:second polymer:third polymer is 1:1:0.75-1.

24. The kit of claim 23, wherein one or more of the first, second, and third polymers are in an aqueous solution or dispersion, wherein the one or more aqueous solutions or dispersions are contained in any suitable vessel.

25. The kit of claim 23, wherein the second and the third polymer are premixed in an aqueous solution or dispersion, and contained in any suitable vessel.

26. The kit of anyone of claim 24, wherein the aqueous solutions or dispersions further comprise one or more additives selected from a group comprising pH modifiers, viscosity modifiers, anti-bacterial agents, anti-microbial agents, colorants, surfactants, and bioreactive agents.

27. The kit of claim 24, wherein the suitable vessel is a syringe barrel.

28. The kit of claim 23, wherein one or more of the first, second, and third polymers are a dried polymer powder.

29. The kit of claim 23, wherein the first and the second polymer are premixed dried polymer powders.

30. The kit of claim 29 further comprising a buffer solution for hydrating the dried polymer powders.

31. The hydrogel of claim 1, wherein the weight ratio of first polymer:second polymer:third polymer is 1:1:1.

32. The method of claim 16, wherein the weight ratio of first polymer:second polymer:third polymer is 1:1:0.75.

33. The hydrogel of claim 16, wherein the weight ratio of first polymer:second polymer:third polymer is 1:1:1.

34. The kit of claim 23, wherein the weight ratio of first polymer:second polymer:third polymer is 1:1:0.75.

35. The kit of claim 23, wherein the weight ratio of first polymer:second polymer:third polymer is 1:1:1.

* * * * *